(12) United States Patent
Baharav et al.

(10) Patent No.: US 7,327,304 B2
(45) Date of Patent: Feb. 5, 2008

(54) SYSTEM AND METHOD FOR MINIMIZING BACKGROUND NOISE IN A MICROWAVE IMAGE USING A PROGRAMMABLE REFLECTOR ARRAY

(75) Inventors: Izhak Baharav, Palo Alto, CA (US); Robert C. Taber, Palo Alto, CA (US); Gregory S. Lee, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 180 days.

(21) Appl. No.: 11/088,830

(22) Filed: Mar. 24, 2005

(65) Prior Publication Data

US 2006/0214834 A1   Sep. 28, 2006

(51) Int. Cl.
*G01S 13/00* (2006.01)
*H01Q 15/00* (2006.01)

(52) U.S. Cl. ............... 342/22; 342/5; 342/27; 342/83; 342/159; 342/179; 342/180

(58) Field of Classification Search ............ 342/22, 342/179, 27
See application file for complete search history.

(56) References Cited

U.S. PATENT DOCUMENTS

| | | | |
|---|---|---|---|
| 4,336,540 A * | 6/1982 | Goodwin et al. | 342/157 |
| 4,502,025 A | 2/1985 | Carl, Jr. et al. | |
| 4,649,393 A | 3/1987 | Rittenbach | |
| 4,885,592 A | 12/1989 | Kofol et al. | |
| 5,027,125 A | 6/1991 | Tang | |
| 5,093,563 A * | 3/1992 | Small et al. | 250/201.9 |
| 5,170,170 A | 12/1992 | Soumekh | |
| 5,365,237 A | 11/1994 | Johnson et al. | |
| 5,621,646 A | 4/1997 | Enge et al. | |
| 5,659,322 A | 8/1997 | Caille | |
| 5,905,473 A * | 5/1999 | Taenzer | 343/834 |
| 5,940,030 A | 8/1999 | Hampel et al. | |
| 5,940,045 A | 8/1999 | Belcher et al. | |
| 5,982,326 A | 11/1999 | Chow et al. | |

(Continued)

FOREIGN PATENT DOCUMENTS

EP    0 031 443    7/1981

(Continued)

OTHER PUBLICATIONS

GB Search Report Under Section 17 dated May 24, 2006.

(Continued)

*Primary Examiner*—Thomas H. Tarcza
*Assistant Examiner*—Harry Liu

(57) ABSTRACT

A microwave imaging system captures a microwave image of a target and minimizes noise in the microwave image using phase differentiation. A reflector antenna array is provided including a plurality of antenna elements for reflecting microwave radiation towards the target and for reflecting microwave radiation reflected from the target towards a microwave receiver. A processor programs the antenna elements with respective first phase shifts to capture a first microwave image of the target, and programs the antenna elements with respective second phase shifts to capture a second microwave image of the target. The first phase shift of each antenna element is 180 degrees different than the second phase shift for that antenna element. The processor minimizes noise from a combination of the first microwave image and the second microwave image.

18 Claims, 4 Drawing Sheets

U.S. PATENT DOCUMENTS

| | | | |
|---|---|---|---|
| 5,986,590 | A | 11/1999 | Smith et al. |
| 6,037,908 | A | 3/2000 | Phillips et al. |
| 6,043,786 | A | 3/2000 | Vannatta et al. |
| 6,057,761 | A | 5/2000 | Yukl |
| 6,242,740 | B1 | 6/2001 | Luukanen et al. |
| 6,353,224 | B1 | 3/2002 | Sinclair et al. |
| 6,501,414 | B2 | 12/2002 | Arndt et al. |
| 6,542,820 | B2 | 4/2003 | LaMance et al. |
| 6,549,166 | B2 | 4/2003 | Bhattacharyya et al. |
| 6,560,534 | B2 | 5/2003 | Abraham et al. |
| 6,642,899 | B2 | 11/2003 | McGrath |
| 6,965,340 | B1 * | 11/2005 | Baharav et al. ............... 342/22 |
| 7,133,644 | B2 * | 11/2006 | Demir et al. ............ 455/67.11 |
| 2003/0034916 | A1 | 2/2003 | Kwon et al. |
| 2003/0189978 | A1 * | 10/2003 | Lin et al. .................... 375/224 |
| 2004/0056790 | A1 | 3/2004 | Lovberg et al. |
| 2004/0080448 | A1 | 4/2004 | Lovberg et al. |
| 2004/0178951 | A1 * | 9/2004 | Ponsford et al. ............ 342/192 |
| 2004/0248516 | A1 * | 12/2004 | Demir et al. .............. 455/63.1 |
| 2005/0018179 | A1 * | 1/2005 | Bevis et al. ............. 356/237.1 |
| 2006/0109174 | A1 * | 5/2006 | Baharav et al. .............. 342/179 |
| 2006/0209978 | A1 * | 9/2006 | Jungnickel et al. ......... 375/267 |
| 2006/0214832 | A1 * | 9/2006 | Lee et al. ..................... 342/22 |
| 2006/0214833 | A1 * | 9/2006 | Baharav et al. ............... 342/22 |
| 2006/0214834 | A1 * | 9/2006 | Baharav et al. ............... 342/22 |
| 2006/0214836 | A1 * | 9/2006 | Baharav et al. ............... 342/22 |

FOREIGN PATENT DOCUMENTS

| | | |
|---|---|---|
| GB | 2313969 | 12/1997 |
| WO | WO 93/05408 | 3/1993 |

OTHER PUBLICATIONS

GB Search Report Under Section 17 dated May 25, 2006.

David M.Sheen et al.; "Three-Dimensional Millimeter-Wave Imaging for Concealed Weapon Detection"; IEEE Transactions On Microwave Theory And Techniques, vol. 49, No. 9, Sep. 2001, pp. 1581-1592.

P.F. Goldsmith, et al.; "Focal Plane Imaging Systems for Millimeter Wavelengths"; IEEE Transactions on Microwave Theory And Techniques, vol. 41, No. 10, Oct. 1993, pp. 1664-1675.

Tatsuo Nozokido, et al.; "Scanning Near-Field Millimeter-Wave Microscopy Using a Metal Slit as a Scanning Probe"; IEEE Transactions On Microwave Theory And Techniques, vol. 49, No. 3, Mar. 2001, pp. 491-499.

Changdon Kee. *Wide Area Differential GPS*. 1994. Standford, California.

Satellite Journal International. *Satellite News NA V1.5*. Apr. 14, 2005. <http://www.sat-net.com/listserver/sat-na/msg00016.html>.

C. Rizos, T. Yan, S. Omar, T. Musa, D. Kinlyside. *Implementing Newtwork-RTK: The SydNET CORS Infrastructure*. The 6th International Symposium on Satellite Navigation Technology Including Mobile Position & Location Services. Jul. 22-25, 2003. Melbourne, Australia.

Orbiter and Radio Metric Systems Group. *Real-Time GIPSY Software*. Apr. 14, 2005. <http://gipsy.jpl.nasa.gov/orms/rtg/index.html>.

OmniSTAR USA, Inc. *OmniSTAR—How It Works*. Apr. 14, 2005. <http://www.ominstar.com/howitworks.html>.

\* cited by examiner

SYSTEM AND METHOD FOR MINIMIZING BACKGROUND NOISE IN A MICROWAVE IMAGE USING A PROGRAMMABLE REFLECTOR ARRAY

CROSS-REFERENCE TO RELATED APPLICATIONS

This application is related by subject matter to U.S. Pat. No. 7,224,314, entitled "A Device for Reflecting Electromagnetic Radiation," U.S. application for patent Ser. No. 10/997,583, entitled "Broadband Binary Phased Antenna," and U.S. application for patent Ser. No. 11/148,079, entitled "System and Method for Security Inspection Using Microwave Imaging," all of which were filed on Nov. 24, 2004.

This application is further related by subject matter to U.S. application for patent Ser. No. 11/088,536, entitled "System and Method for Efficient, High-Resolution Microwave Imaging Using Complementary Transmit and Receive Beam Patterns," U.S. Pat. No. 7,183,963, application for patent Ser. No. entitled "System and Method for Inspecting Transportable Items Using Microwave Imaging," U.S. application for patent Ser. No. 11/089,298, entitled "System and Method for Pattern Design in Microwave Programmable Arrays," and U.S. application for patent Ser. No. 11/088,610, entitled "System and Method for Microwave Imaging Using an Interleaved Pattern in a Programmable Reflector Array," all of which were filed on even date herewith.

BACKGROUND OF THE INVENTION

Recent advances in microwave imaging have enabled commercial development of microwave imaging systems that are capable of generating two-dimensional and even three-dimensional microwave images of objects and other items of interest (e.g., human subjects). At present, there are several microwave imaging techniques available. For example, one technique uses an array of microwave detectors (hereinafter referred to as "antenna elements") to capture either passive microwave radiation emitted by a target associated with the person or other object or reflected microwave radiation reflected from the target in response to active microwave illumination of the target. A two-dimensional or three-dimensional image of the person or other object is constructed by scanning the array of antenna elements with respect to the target's position and/or adjusting the frequency (or wavelength) of the microwave radiation being transmitted or detected.

Microwave imaging systems typically include transmit, receive and/or reflect antenna arrays for transmitting, receiving and/or reflecting microwave radiation to/from the object. Such antenna arrays can be constructed using traditional analog phased arrays or binary reflector arrays. In either case, the antenna array typically directs a beam of microwave radiation towards a point in 3D space corresponding to a voxel in an image of the object, hereinafter referred to as a target. This is accomplished by programming each of the antenna elements in the array with a respective phase shift. Examples of programmable antenna arrays are described in U.S. Pat. No. 7,224,314, entitled "A Device for Reflecting Electromagnetic Radiation," and Ser. No. 10/997,583, entitled "Broadband Binary Phased Antenna."

When using reflector antenna arrays, a typical microwave imaging system includes a microwave source, a microwave receiver, which may be co-located with the microwave source, and one or more reflector antenna arrays. Microwave radiation transmitted from the source is received at the reflector antenna array and reflected towards a target by programming each of the reflecting antenna elements in the array with a respective phase shift. Likewise, reflected microwave radiation reflected from the target and received by the array is reflected towards the microwave receiver by programming each of the individual reflecting antenna elements with a respective phase shift. The microwave receiver combines the received microwave radiation reflected from each antenna element in the array to produce a value of the effective intensity of the reflected microwave radiation at the target, which represents the value of a pixel or voxel corresponding to the target on the object.

However, some of the microwave radiation from the source is reflected off of the array and directly transmitted towards the microwave receiver without reflecting off the target. In addition, some of the microwave radiation from the source is scattered off of various undesired points in 3D space (e.g., other targets on the object being imaged or other objects) towards the array, and reflected back to the microwave receiver. Such stray microwave radiation contributes to the background noise (often referred to as "clutter"), and reduces the signal-to-noise ratio (SNR) of the microwave imaging system. What is needed is a mechanism for minimizing the background noise in a microwave image captured using a programmable reflector array.

SUMMARY OF THE INVENTION

Embodiments of the present invention provide a microwave imaging system for capturing a microwave image of a target and minimizing noise in the microwave image using phase differentiation. A reflector antenna array is provided including a plurality of antenna elements for reflecting microwave radiation towards the target and for reflecting microwave radiation reflected from the target towards a microwave receiver. A processor programs the antenna elements with respective first phase shifts to capture a first microwave image of the target, and programs the antenna elements with respective second phase shifts to capture a second microwave image of the target. The first phase shift of each antenna element is 180 degrees different than the second phase shift for that antenna element. The processor minimizes noise from a combination of the first microwave image and the second microwave image.

In one embodiment, the microwave radiation received at the microwave receiver includes both double-reflected microwave radiation reflected by the array from a microwave source to the target and from the target to the microwave receiver and single-reflected microwave radiation reflected by the array from the microwave source to the microwave receiver without first being reflected by the array from the microwave source to the target. The phase of the double-reflected microwave radiation in the first microwave image is the same as the phase of the double-reflected microwave radiation in the second microwave image. However, the phase of the single-reflected microwave radiation in the first microwave image is 180 degrees different than the phase of the single-reflected microwave radiation in the second microwave image.

In another embodiment, the processor adds the first microwave image and the second microwave image to produce a final microwave image including only the double-reflected microwave radiation of both the first microwave image and the second microwave image. By adding the first and second microwave images together, the processor is able to remove the single-reflected microwave radiation, corresponding to a noise component, from the final microwave image. The noise component can be determined during a calibration of the microwave imaging system for later use in correcting microwave images.

BRIEF DESCRIPTION OF THE DRAWINGS

The disclosed invention will be described with reference to the accompanying drawings, which show important sample embodiments of the invention and which are incorporated in the specification hereof by reference, wherein.

DETAILED DESCRIPTION OF THE EXEMPLARY EMBODIMENTS

As used herein, the terms microwave radiation and microwave illumination each refer to the band of electromagnetic radiation having wavelengths between 0.3 mm and 30 cm, corresponding to frequencies of about 1 GHz to about 1,000 GHz. Thus, the terms microwave radiation and microwave illumination each include traditional microwave radiation, as well as what is commonly known as millimeter-wave radiation.

Figure 1:
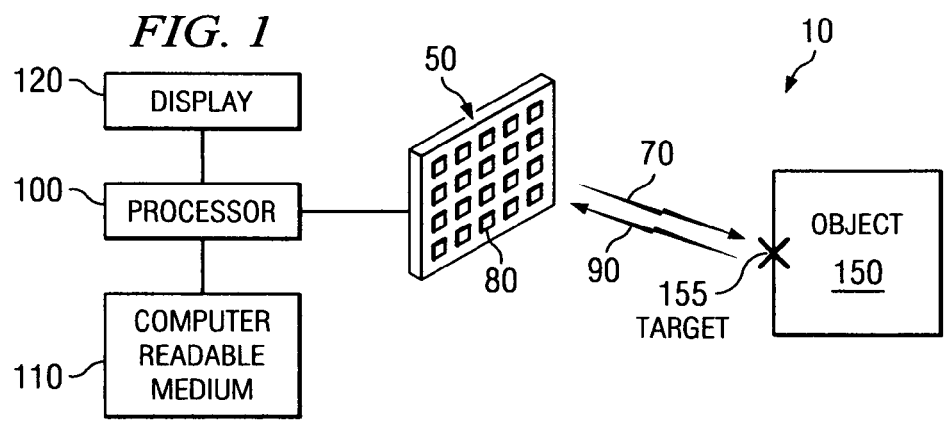
FIG. 1 is a schematic diagram of a simplified exemplary microwave imaging system including a programmable antenna array in accordance with embodiments of the present invention.

FIG. 1 is a schematic diagram of a simplified exemplary microwave imaging system 10, in accordance with embodiments of the present invention. The microwave imaging system 10 includes a one or more arrays 50 (only one of which is shown for convenience), each capable of transmitting microwave radiation and/or receiving microwave radiation via antenna elements 80 to capture a microwave image of an object (e.g., suitcase, human subject or any other item of interest).

In one embodiment, the array 50 includes a passive programmable reflector array composed of reflecting antenna elements 80. Each of the reflecting antenna elements is capable of being programmed with a respective phase shift to direct a beam of microwave radiation towards a target 155 on the object 150 being imaged. The phase shift can be either binary or continuous. For example, microwave radiation received by the array 50 from a microwave source (not shown) is reflected towards the target 155 on the object 150, and reflected microwave radiation reflected from the target 155 and received by the array 50 is reflected towards microwave receiver (not shown) by programming each of the individual reflecting antenna elements 80 with a respective phase shift.

The microwave imaging system 10 further includes a processor 100, computer-readable medium 110 and a display 120. The processor 100 includes any hardware, software, firmware, or combination thereof for controlling the array 50 and processing the received microwave radiation reflected from the target 155 to construct a microwave image of the target 155 and/or object 150. For example, the processor 100 may include one or more microprocessors, microcontrollers, programmable logic devices, digital signal processors or other type of processing devices that are configured to execute instructions of a computer program, and one or more memories (e.g., cache memory) that store the instructions and other data used by the processor 100. However, it should be understood that other embodiments of the processor 100 may be used. The memory 110 is any type of data storage device, including but not limited to, a hard drive, random access memory (RAM), read only memory (ROM), compact disc, floppy disc, ZIP® drive, tape drive, database or other type of storage device or storage medium.

The processor 100 operates to program the phase delays or phase shifts of each of the individual antenna elements 80 in the array 50 to illuminate multiple targets 155 on the object 150 with microwave radiation and/or receive reflected microwave illumination from multiple targets 155 on the object 150. Thus, the processor 100 in conjunction with the array 50 operates to scan the object 150.

The processor 100 is further capable of constructing a microwave image of the object 150 using the intensity of the reflected microwave radiation captured by the array 50 from each target 155 on the object 150. For example, in embodiments where the array 50 is a reflector array, the microwave receiver (not shown) is capable of combining the reflected microwave radiation reflected from each antenna element 80 in the array 50 to produce a value of the effective intensity of the reflected microwave radiation at the target 155. The intensity value is passed to the processor 100, which uses the intensity value as the value of a pixel or voxel corresponding to the target 155 on the object 150. In operation, the microwave imaging system 10 can operate at frequencies that enable millions of targets 155 to be scanned per second.

The resulting microwave image of the target 155 and/or object 150 can be passed from the processor 100 to the display 120 to display the microwave image. In one embodiment, the display 120 is a two-dimensional display for displaying a three-dimensional microwave image of the object 30 or one or more one-dimensional or two-dimensional microwave images of the target 155 and/or object 150. In another embodiment, the display 120 is a three-dimensional display capable of displaying a three-dimensional microwave image of the object 150.

It should be understood that multiple arrays 50 may be used to scan different portions of the object 150. For example, the microwave imaging system 10 can be implemented with two arrays, each including a 1 m×1 m array of antenna elements 80 to scan half of the object 150, when the object 150 is a person of height 2 meters and width 1 meter. As another example, the microwave imaging system 10 can be implemented with eight arrays 50, each including a 0.5 m×0.5 m array of antenna elements 80 capable of scanning a quadrant of the person object 150.

Figure 2:
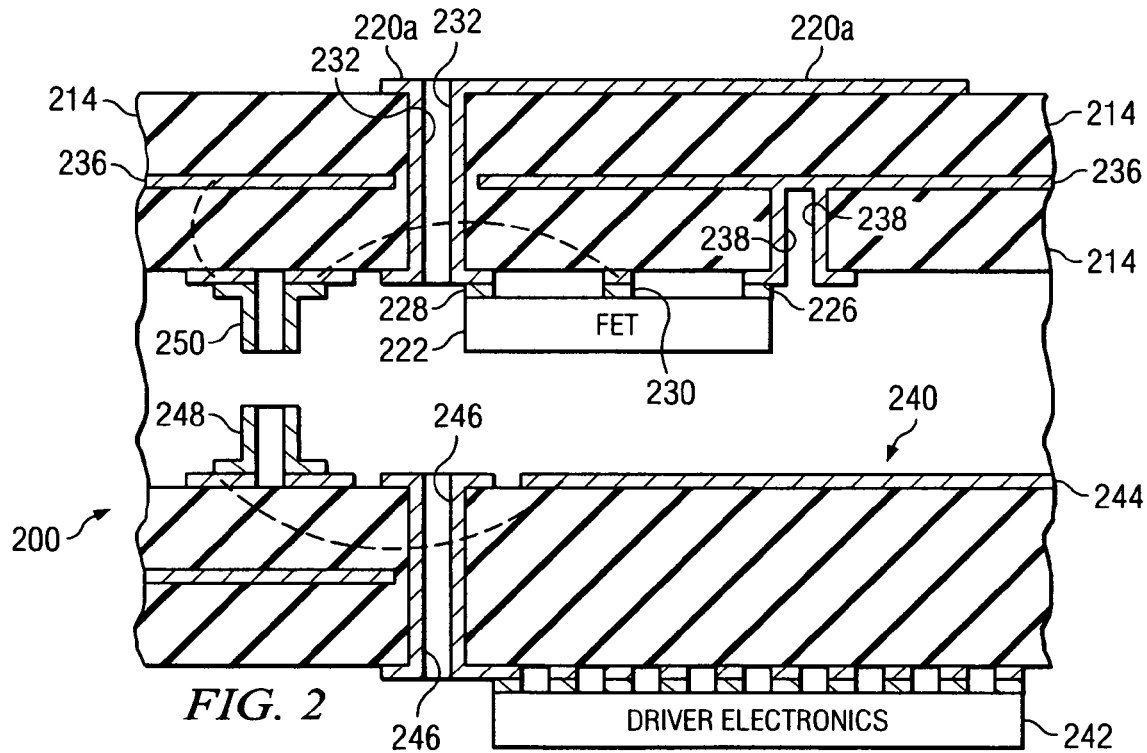
FIG. 2 is a cross-sectional view of a passive antenna element for use in a reflector array, in accordance with embodiments of the present invention.

FIG. 2 illustrates a cross-sectional view of a reflecting antenna element 200 (corresponding to antenna element 80 in FIG. 1) that operates to reflect electromagnetic radiation with varying phase depending on the impedance state of the antenna element 200. The reflecting antenna element 200 includes an antenna (patch antenna 220a) and a non-ideal switching device (surface mounted field effect transistor "FET" 222).

The reflecting antenna element 200 is formed on and in a printed circuit board substrate 214 and includes the surface mounted FET 222, the patch antenna 220a, a drain via 232, a ground plane 236 and a source via 238. The surface mounted FET 222 is mounted on the opposite side of the printed circuit board substrate 214 as the planar patch antenna 220a and the ground plane 236 is located between the planar patch antenna 220a and the surface mounted FET 222. The drain via 232 connects the drain 228 of the surface mounted FET 222 to the planar patch antenna 220a and the source via 238 connects the source 226 of the surface mounted FET 222 to the ground plane 236.

In a working product, the reflector antenna array is connected to a controller board 240 that includes driver electronics. An example controller board 240 is also depicted in FIG. 2 and includes a ground plane 244, a drive signal via 246, and driver electronics 242. The controller board 240 also includes connectors 248 that are compatible with connectors 250 of the reflector antenna array. The connectors 248 and 250 of the two boards can be connected to each other, for example, using wave soldering. It should be understood that in other embodiments, the FET 222 can be surface mounted on the same side of the printed circuit board substrate 214 as the planar patch antenna 220a. Additionally, the driver electronics 242 can be soldered directly to the same printed circuit board in which the reflecting antenna element 200 is built.

The patch antenna element 220a functions to reflect with more or less phase shift depending on the impedance level of the reflecting antenna element 200. The reflecting antenna element 200 has an impedance characteristic that is a function of the antenna design parameters. Design parameters of antennas include but are not limited to, physical attributes such as the dielectric material of construction, the thickness of the dielectric material, shape of the antenna, length and width of the antenna, feed location, and thickness of the antenna metal layer.

The FET 230 (non-ideal switching device) changes the impedance state of the reflecting antenna element 200 by changing its resistive state. A low resistive state (e.g., a closed or "short" circuit) translates to a low impedance. Conversely, a high resistive state (e.g., an open circuit) translates to a high impedance. A switching device with ideal performance characteristics (referred to herein as an "ideal" switching device) produces effectively zero impedance (Z=0) when its resistance is at its lowest state and effectively infinite impedance (Z=∞) when its resistance is at its highest state. As described herein, a switching device is "on" when its impedance is at its lowest state (e.g., $Z_{on}=0$) and "off" when its impedance is at its highest state (e.g., $Z_{off}=\infty$). Because the on and off impedance states of an ideal switching device are effectively $Z_{on}=0$ and $Z_{off}=\infty$, an ideal switching device is able to provide the maximum phase shift without absorption of electromagnetic radiation between the on and off states. That is, the ideal switching device is able to provide switching between 0 and 180 degree phase states. In the case of an ideal switching device, maximum phase-amplitude performance can be achieved with an antenna that exhibits any finite non-zero impedance.

In contrast to an ideal switching device, a "non-ideal" switching device is a switching device that does not exhibit on and off impedance states of $Z_{on}=0$ and $Z_{off}=\infty$, respectively. Rather, the on and off impedance states of a non-ideal switching device are typically, for example, somewhere between $0<|Z_{on}|<|Z_{off}|<\infty$. However, in some applications, the on and off impedance states may even be $|Z_{off}|<=|Z_{on}|$. A non-ideal switching device may exhibit ideal impedance characteristics within certain frequency ranges (e.g., <10 GHz) and highly non-ideal impedance characteristics at other frequency ranges (e.g., >20 GHz).

Because the on and off impedance states of a non-ideal switching device are somewhere between $Z_{on}=0$ and $Z_{off}=\infty$, the non-ideal switching device does not necessarily provide the maximum phase state performance regardless of the impedance of the corresponding antenna, where maximum phase state performance involves switching between 0 and 180 degree phase states. In accordance with the invention, the reflecting antenna element 200 of FIG. 2 is specifically designed to provide optimal phase performance, where the optimal phase state performance of a reflecting antenna element is the point at which the reflecting element is closest to switching between 0 and 180 degree phase-amplitude states. In an embodiment, to achieve optimal phase state performance, the antenna element 200 is configured as a function of the impedance of the non-ideal switching device (FET 230). For example, the antenna element 200 is designed such that the impedance of the antenna element 200 is a function of impedance characteristics of the FET 230.

Further, the antenna element 200 is configured as a function of the impedance of the non-ideal switching device (FET 230) in the on state, $Z_{on}$, and the impedance of the non-ideal switching device 230 in the off state, $Z_{off}$. In a particular embodiment, the phase state performance of the reflecting antenna element 200 is optimized when the antenna element 200 is configured such that the impedance of the antenna element 200 is conjugate to the square root of the impedance of the non-ideal switching device 230 when in the on and off impedance states, $Z_{on}$ and $Z_{off}$. Specifically, the impedance of the antenna element 200 is the complex conjugate of the geometric mean of the on and off impedance states, $Z_{on}$ and $Z_{off}$, of the corresponding non-ideal switching device 230. This relationship is represented as:

$$Z_{antenna}{}^* = \sqrt{Z_{on} Z_{off}}, \qquad (1)$$

where ( )* denotes a complex conjugate. The above-described relationship is derived using the well-known formula for the complex reflection coefficient between a source impedance and a load impedance. Choosing the source to be the antenna element 200 and the load to be the non-ideal switching device 230, the on-state reflection coefficient is set to be equal to the opposite of the off-state reflection coefficient to arrive at equation (1).

Designing the antenna element 200 to exhibit optimal phase-amplitude performance involves determining the on and off impedances, $Z_{on}$ and $Z_{off}$ of the particular non-ideal switching device that is used in the reflecting antenna element 200 (in this case, FET 230). Design parameters of the antenna element 200 are then manipulated to produce an antenna element 200 with an impedance that matches the relationship expressed in equation (1) above. An antenna element 200 that satisfies equation (1) can be designed as long as $Z_{on}$ and $Z_{off}$ are determined to be distinct values.

Another type of switching device, other than the surface mounted FET 230 shown in FIG. 2, that exhibits non-ideal impedance characteristics over the frequency band of interest is a surface mount diode. However, although surface mounted diodes exhibit improved impedance characteristics over the frequency band of interest compared to surface mounted FETs, surface mounted FETs are relatively inexpensive and can be individually packaged for use in reflector antenna array applications.

In a reflector antenna array that utilizes FETs as the non-ideal switching devices, the beam-scanning speed that can be achieved depends on a number of factors including signal-to-noise ratio, crosstalk, and switching time. In the case of a FET, the switching time depends on gate capacitance, drain-source capacitance, and channel resistance (i.e., drain-source resistance). The channel resistance is actually space-dependent as well as time-dependent. In order to minimize the switching time between impedance states, the drain of the FET is preferably DC-shorted at all times. The drain is preferably DC-shorted at all times because floating the drain presents a large off-state channel resistance as well as a large drain-source capacitance due to the huge parallel-plate area of the patch antenna. This implies that the antenna is preferably DC-shorted but one wishes the only "rf short" the antenna sees be at the source. Therefore, the additional antenna/drain short must be optimally located so as to minimally perturb the antenna.

It should be understood that other types of antennas can be used in the reflecting antenna element 200, instead of the patch antenna 220a. By way of example, but not limitation, other antenna types include dipole, monopole, loop, and dielectric resonator type antennas. In addition, in other embodiments, the reflecting antenna element 200 can be a continuous phase-shifted antenna element 200 by replacing the FETs 230 with variable capacitors (e.g., Barium Strontium Titanate (BST) capacitors). With the variable capacitor loaded patches, continuous phase shifting can be achieved for each antenna element 200, instead of the binary phase shifting produced by the FET loaded patches. Continuous phased arrays can be adjusted to provide any desired phase shift in order to steer a microwave beam towards any direction in a beam scanning pattern.

Figure 3:
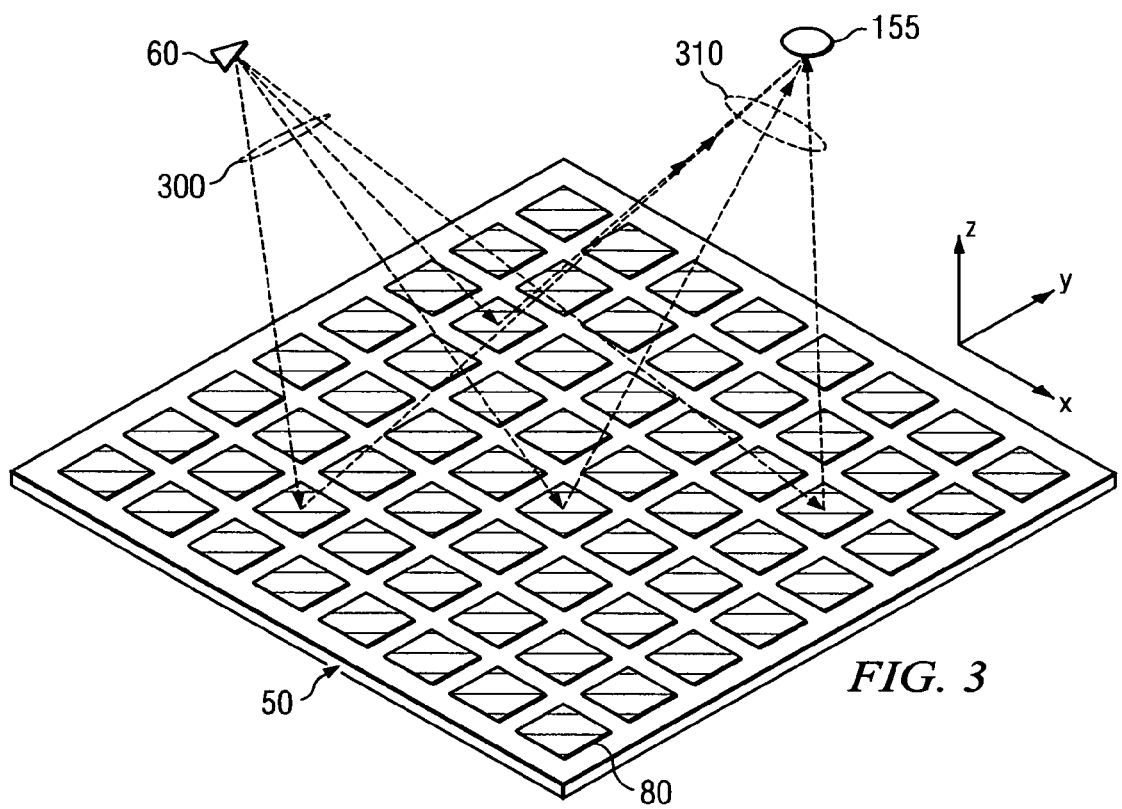
FIG. 3 is a schematic diagram of a top view of an exemplary reflector array incorporating reflecting antenna elements for reflecting microwave radiation, in accordance with embodiments of the present invention.

FIG. 3 is a schematic diagram of a top view of an exemplary array 50 for reflecting microwave radiation, in accordance with embodiments of the present invention. In FIG. 3, a source beam 300 of microwave radiation transmitted from a microwave source 60 is received by various antenna elements 80 in the array 50. The microwave source can be any source sufficient for illuminating the array 50, including, but not limited to, a point source, a horn antenna or any other type of antenna. The antenna elements 80 within the array 50 are each programmed with a respective phase shift to direct a transmit beam 310 of reflected microwave radiation towards a target 155. The phase shifts are selected to create positive interference of the reflected microwave illumination 310 from each of the antenna elements 80 at the target 155. Ideally, the phase shift of each of the antenna elements 80 is adjusted to provide the same phase delay for each path of the reflected microwave illumination 310 from the source (antenna element 80) to the target 155.

Figure 4:
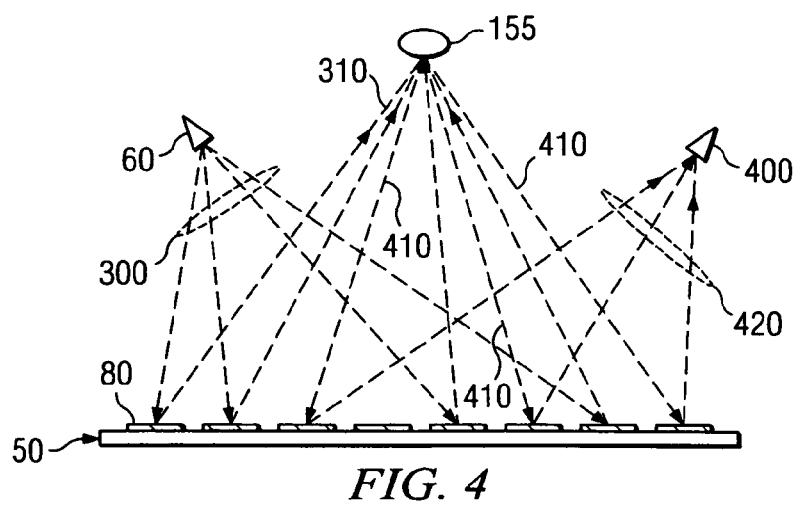
FIG. 4 is a schematic diagram illustrating the reflection of microwave radiation between a microwave source and a microwave receiver using a programmable antenna array in accordance with embodiments of the present invention.

In a similar manner, as shown in FIG. 4, a reflect beam 410 of microwave radiation reflected from the target 155 and received at the array 50 can be reflected as a receive beam 420 of reflected microwave radiation towards a microwave receiver 400. Although the microwave receiver 400 is shown at a different spatial location than the microwave source 60, it should be understood that in other embodiments, the microwave source 60 can be positioned in the same spatial location as the microwave receiver 400 as a separate antenna or as part of the microwave receiver 400 (e.g., a confocal imaging system).

Figure 5:
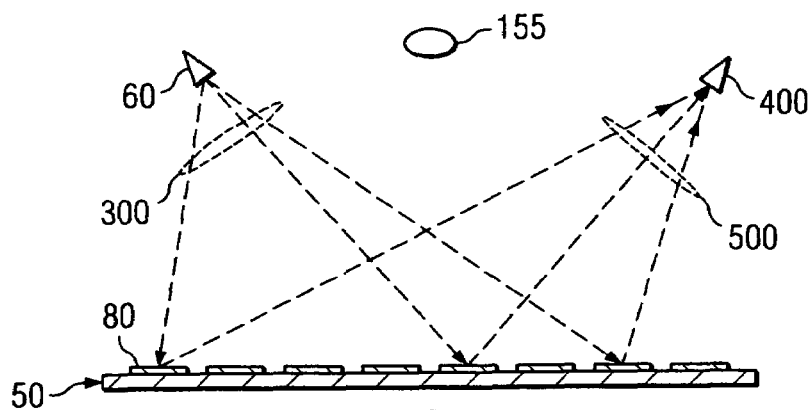
FIG. 5 is a schematic diagram illustrating leakage microwave radiation directly between a microwave source and a microwave receiver.

As discussed above, background noise resulting from stray radiation from the microwave source to the microwave receiver reduces the signal-to-noise ratio (SNR) of the microwave imaging system. Referring now to FIG. 5, there is illustrated exemplary leakage (stray) microwave radiation between a microwave source 60 and a microwave receiver 400. As in FIG. 4, a source beam 300 of microwave radiation transmitted from the microwave source (antenna) 60 is received by various antenna elements 80 in the array 50. The antenna elements 80 are each programmed with a respective phase shift to reflect a transmit beam 310 of microwave radiation towards a target 155. However, some of the microwave radiation in the source beam 300 is reflected off of the array 50 in a stray beam 500 of stray microwave radiation towards the microwave receiver 400. In addition, although not shown, it should be understood that the stray beam 500 of stray microwave radiation also includes other sources of stray microwave radiation. For example, the stray beam 500 also includes microwave radiation scattered off of various undesired points in 3D space (e.g., other targets on the object being imaged or other objects) towards the array, and reflected back to the microwave receiver 400. This stray microwave radiation 500 can reduce the quality of the resulting microwave image by decreasing the SNR.

Figure 6A:
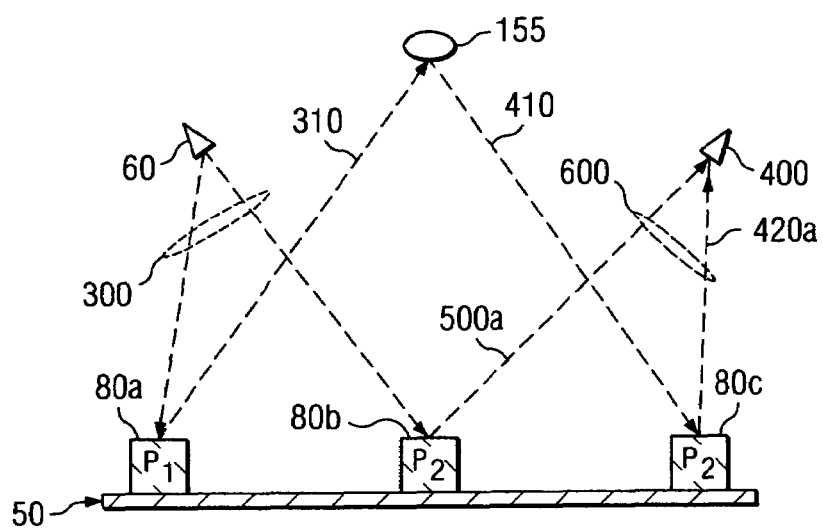
FIGS. 6A and 6B are schematic diagrams illustrating phase shift changes between two successive microwave images, each taken from microwave radiation containing both a signal and noise, in accordance with embodiments of the present invention.
Figure 6B:
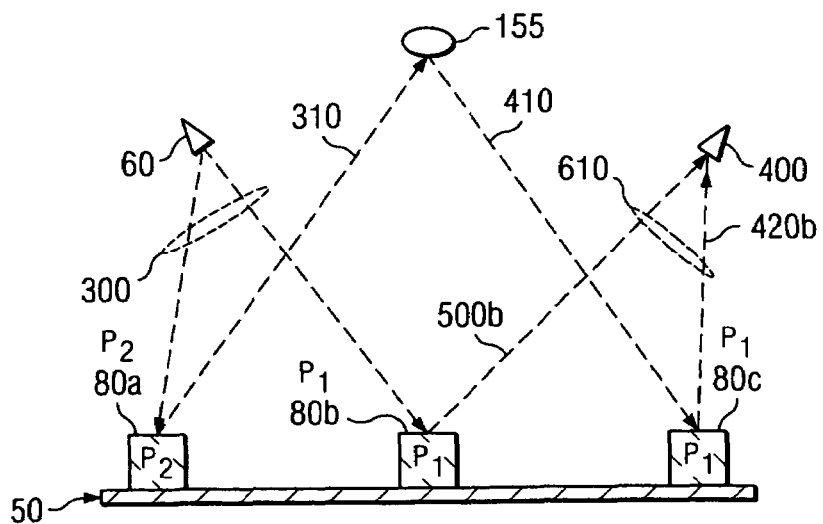

In accordance with embodiments of the present invention, the noise in the microwave image is minimized by removing the stray microwave radiation using phase differentiation. FIGS. 6A and 6B illustrate an example of phase differentiation between successive microwave images to isolate and remove noise from the microwave images. As can be seen in FIG. 6A, the microwave source 60 transmits a source beam 300 of microwave radiation towards various antenna elements 80a and 80b in the array 50. Each of the antenna elements 80a and 80b are programmed with a respective first phase shift to reflect a transmit beam 310 of microwave radiation towards a target 155. For example, antenna element 80a is programmed with a first phase shift of P1 and antenna element 80b is programmed with a first phase shift of P2. For simplicity, a binary array 50 capable of producing only two different phase shifts (e.g., 0 degrees and 180 degrees) is shown in FIGS. 6A and 6B. Thus, for example, P1 may correspond to a phase shift of 0 degrees and P2 may correspond to a phase shift of 180 degrees. However, it should be understood that embodiments of the present invention are equally applicable to other quantized arrays and continuously-phased arrays.

In FIG. 6A, the microwave radiation 310 reflected from antenna element 80a towards the target 155 is reflected back from the target 155 towards the array 50 as reflected microwave radiation 410. The reflected microwave radiation 410 is received at antenna element 80c, which is programmed with a first phase shift, P2, to reflect the reflected microwave radiation 410 towards the microwave receiver 400 as double-reflected microwave radiation 420a. However, not all of the reflected radiation is transmitted from 80a and 80b to the target, but rather some of the microwave radiation is reflected directly towards the receiver as stray (single-reflected) microwave radiation 500a. As used herein, the term "single-reflected microwave radiation" includes both stray microwave radiation transmitted directly from the microwave source 60 to the array 50, and then directly to the microwave receiver 400, and stray microwave radiation reflected off of undesired scatterers towards the array 50, and then directly to the microwave receiver 400. Thus, a beam 600 of reflected microwave radiation received at the microwave receiver 400 includes both double-reflected microwave radiation 420a (signal) and single-reflected microwave radiation 500a (noise). As a result, the microwave image captured using the beam 600 of microwave radiation includes a noise element.

To minimize the noise element in the microwave image, an additional microwave image of the target is captured by programming the antenna elements 80a-80c with respective second phase shifts that are each 180 degrees different than the first phase shift programmed for that antenna element 80a-80c. For example, antenna element 80a is programmed with a second phase shift of P2 and antenna element 80b is programmed with a second phase shift of P1. Again, the microwave radiation 310 reflected from antenna element 80a towards the target 155 is reflected back from the target 155 towards the array 50 as reflected microwave radiation 410. The reflected microwave radiation 410 is received at antenna element 80c, which is programmed with the second phase shift of P1 to reflect the reflected microwave radiation 410 towards the microwave receiver 400 as double-reflected microwave radiation 420b. In addition, part of the microwave radiation received at antenna element 80b is reflected directly towards the receiver as stray (single-reflected) microwave radiation 500b. Thus, a beam 610 of reflected microwave radiation received at the microwave receiver 400 includes both double-reflected microwave radiation 420b (signal) and single-reflected microwave radiation 500b (noise).

Comparing FIGS. 6A and 6B, it can be seen that the first phase shift programmed for antenna element 80a is P1 (e.g., 0 degrees) and the second phase shift programmed for antenna element 80a is P2 (e.g., 180 degrees), which is opposite in phase from P1. Likewise, the first phase shift programmed for antenna element 80b is P2 (e.g., 180 degrees) and the second phase shift programmed for antenna element 80b is P1 (e.g., 0 degrees), which is opposite in phase from P2. Therefore, the microwave radiation received at antenna element 80b and reflected directly towards the receiver as stray (single-reflected) microwave radiation 500b in FIG. 6B is shifted in phase 180 degrees from the single-reflected microwave radiation 500a in FIG. 6A. However, the double-reflected microwave radiation 420b in FIG. 6B has the same phase as the double-reflected microwave radiation 420a in FIG. 6A. Since the double-reflected microwave radiation 420b is reflected twice off the array 50, the total phase shift experienced by the double-reflected microwave radiation 420b in FIG. 6B is the same as that experienced by the double-reflected microwave radiation 420a in FIG. 6A.

For example, assuming a phase shift of P1 corresponds to a 0 degree phase shift and a phase shift of P2 corresponds to a 180 degree phase shift, the microwave radiation 300 received at antenna element 80a in FIG. 6A is reflected with a 0 degree phase shift towards the target 155. The reflected microwave radiation 410 reflected from the target 155 and received at antenna element 80c is reflected towards the microwave receiver 400 with a 180 degree phase shift. Thus, the total phase shift experienced by the double-reflected microwave radiation 420a is 180 degrees. Likewise, in FIG. 6B, the microwave radiation 300 received at antenna element 80a in FIG. 6B is reflected with a 180 degree phase shift towards the target 155. The reflected microwave radiation 410 reflected from the target 155 and received at antenna element 80c is reflected towards the microwave receiver 400 with a 0 degree phase shift. Thus, the total phase shift experienced by the double-reflected microwave radiation 420b is also 180 degrees. From these two microwave images taken with the phase of all antenna elements 80 in the array 50 shifted 180 degrees between the two images, the noise can be removed from the first microwave image.

In one embodiment, the switching of phase shifts between the first microwave image and the second microwave image can be implemented by separately programming the individual antenna elements 80 with different phase shift patterns for each microwave image. In another embodiment, each antenna element 80 can include logic to switch between the first phase shift and the second phase shift. For example, with a binary array where the phase shifts correspond to either a logic state of "1" or a logic state of "0", instead of loading a new pattern into the array for the second microwave image, each antenna element 80 can include logic that will switch the logic state of the antenna element 80 from a "1" to a "0" or vice-versa between the first and second images.

Figure 7:
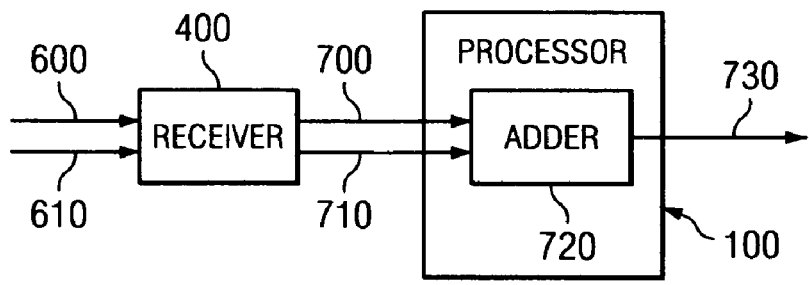
FIG. 7 is a block diagram illustrating the processing components for removing noise from a microwave image of a target, in accordance with embodiments of the present invention.

FIG. 7 is a block diagram illustrating the processing components for removing noise from a microwave image of a target, in accordance with embodiments of the present invention. As described above in connection with FIGS. 6A and 6B, the microwave receiver 400 receives a first beam 600 of microwave radiation and a second beam 610 of microwave radiation. Each beam 600 and 610 contains both a signal component (e.g., double-reflected microwave radiation 420a and 420b shown in FIGS. 6A and 6B) and a noise component (e.g., single-reflected microwave radiation 500a and 500b shown in FIGS. 6A and 6B). The measured intensity 700 and 710 of each beam 600 and 610, respectively, is input to an adder 720 in the processor 100 to add the first measured intensity 700 corresponding to the first microwave image with the second measured intensity 710 corresponding to the second microwave image.

Since the total phase shift experienced by the double-reflected microwave radiation (signal component) in each beam 600 and 610 is the same, the addition performed by the adder 720 sums the signal components in both beams 600 and 610. However, since the single-reflected microwave radiation (noise component) in each beam 600 and 610 experiences a 180 degree phase shift between the two beams 600 and 610, the addition performed by the adder 720 removes the noise component (i.e., the noise component is canceled out). The result produced by the adder 720 is a final microwave image 730, which includes the signal component of both beams 600 and 610. Thus, the final microwave image 730 corresponds to the microwave image that would result from the reflected microwave radiation 420 in FIG. 4 without any noise present in the system.

In one embodiment, the total exposure time for the combination of the first beam 600 and the second beam 610 is substantially equal to the total integration time of the microwave receiver 400. Since the signal components of each beam 600 and 610 are added together, the integration time of each signal component is added together to form a complete integration time necessary for the receiver to capture the final microwave image 730 of the target. Thus, the two phase-shifted microwave images can be taken within the time frame of a single microwave image.

It should be understood that in one embodiment, the noise removing mechanism described above is implemented for each microwave image taken by the microwave imaging system. In other embodiments, the noise removing mechanism is implemented during a calibration of the microwave imaging system, and the noise component determined during the calibration process is used in subsequent measurements performed by the microwave imaging system to correct the microwave images taken by the microwave imaging system.

Figure 8:
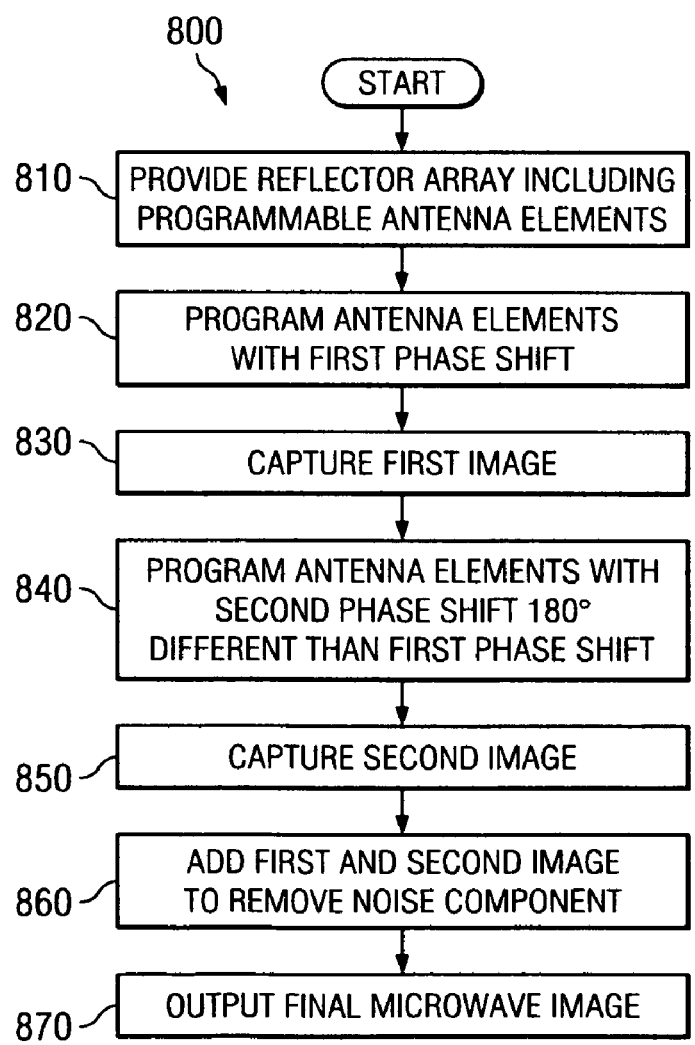
FIG. 8 is a flow chart illustrating an exemplary process for removing noise from a microwave image of a target, in accordance with embodiments of the present invention.

FIG. 8 is a flow chart illustrating an exemplary process 800 for optimizing a microwave imaging system for capturing a microwave image of a target, in accordance with embodiments of the present invention. Initially, an array of programmable microwave antenna elements is provided at block 810. At block 820, each of the antenna elements in the array is programmed with a respective first phase shift to direct a beam of microwave radiation towards a target. At block 830, a first microwave image of the target is captured.

Thereafter, at block 840, the programmed phase shift of each of the antenna elements is flipped 180 degrees in order to capture a second microwave image of the target at block 850. The first and second microwave images are added together at block 860 to remove a noise component from the images and produce a final microwave image containing only the signal component from the first and second microwave images. At block 870, the final microwave image is output as the microwave image of the target.

As will be recognized by those skilled in the art, the innovative concepts described in the present application can be modified and varied over a wide rage of applications. Accordingly, the scope of patents subject matter should not be limited to any of the specific exemplary teachings discussed, but is instead defined by the following claims.

We claim:

1. A microwave imaging system for capturing a microwave image of a target, comprising:
   a microwave source for providing microwave radiation;
   a microwave receiver for receiving microwave radiation;
   a reflector antenna array including a plurality of antenna elements, each of said antenna elements being capable of being programmed with a respective phase shift to reflect the microwave radiation towards the target in a transmit beam and reflect a receive beam of microwave illumination reflected from the target towards said microwave receiver; and
   a processor operable to program said plurality of antenna elements with respective first phase shifts to capture a first microwave image of the target and to program said plurality of antenna elements with respective second phase shifts to capture a second microwave image of the target, said first phase shifts and said second phase shifts of each of said respective plurality of antenna elements being different by 180 degrees;
   wherein said processor is further operable to minimize noise from a combination of said first microwave image and said second microwave image.

2. The system of claim 1, wherein each of said plurality of antenna elements are binary phase-shifted antenna elements.

3. The system of claim 1, wherein said receive beam includes double-reflected microwave radiation reflected by said array from said microwave source to the target and from the target to said microwave receiver and single-reflected microwave radiation reflected by said array to said microwave receiver without first being reflected by said array from said microwave source to the target.

4. The system of claim 3, wherein the phase of said double-reflected microwave radiation in said first microwave image is the same as the phase of said double-reflected microwave radiation in said second microwave image, and wherein the phase of said single-reflected microwave radiation in said first microwave image is 180 degrees different than the phase of said single-reflected microwave radiation in said second microwave image.

5. The system of claim 4, wherein said processor is further operable to add said first microwave image and said second microwave image to produce a final microwave image including only said double-reflected microwave radiation of both said first microwave image and said second microwave image, said double-reflected microwave radiation of both said first microwave image and said second microwave image corresponding to a signal component.

6. The system of claim 5, wherein said processor is further operable to remove said single-reflected microwave radiation from said final microwave image by adding said first microwave image and said second microwave image, said single-reflected microwave radiation removed from said final microwave image corresponding to a noise component.

7. The system of claim 6, wherein said processor is further operable to determine said noise component during a calibration of said microwave imaging system.

8. The system of claim 1, wherein said array includes logic for each of said plurality of antenna elements configured to switch between said first phase shift and said second phase shift.

9. The system of claim 1, wherein a total exposure time for a combination of said first microwave image and said second microwave image is substantially equivalent to an integration time of said microwave receiver.

10. A method for minimizing noise in a microwave image of a target, comprising:
    providing an array including a plurality of antenna elements, each of said antenna elements being capable of being programmed with a respective phase shift to reflect microwave radiation towards the target in a transmit beam and reflect a receive beam of microwave illumination reflected from the target towards a microwave receiver;
    programming said plurality of antenna elements with respective first phase shifts to capture a first microwave image of the target;
    programming said plurality of antenna elements with respective second phase shifts to capture a second microwave image of the target, said first phase shifts and said second phase shifts of each of said respective plurality of antenna elements being 180 degrees apart; and
    minimizing noise from a combination of said first microwave image and said second microwave image.

11. The method of claim 10, wherein each of said plurality of antenna elements are binary phase-shifted antenna elements.

12. The method of claim 10, wherein said receive beam includes double-reflected microwave radiation reflected by said array from said microwave source to the target and from the target to said microwave receiver and single-reflected microwave radiation reflected by said array from said microwave source to said microwave receiver without first being reflected by said array from said microwave source to the target.

13. The method of claim 12, wherein the phase of said double-reflected microwave radiation in said first microwave image is the same as the phase of said double-reflected microwave radiation in said second microwave image, and wherein the phase of said single-reflected microwave radiation in said first microwave image is 180 degrees different than the phase of said single-reflected microwave radiation in said second microwave image.

14. The method of claim 13, wherein said minimizing the noise further includes adding said first microwave image and said second microwave image to produce a final microwave image including only said double-reflected microwave radiation of both said first microwave image and said second microwave image.

15. The method of claim 10, wherein said minimizing the noise further includes adding said first microwave image and said second microwave image to determine a noise component.

16. The method of claim 15, wherein said minimizing the noise further includes calibrating a microwave imaging system including said array to determine the noise component.

17. The method of claim 10, further comprising: switching between said first phase shift and said second phase shift within said array to capture said second microwave image.

18. The method of claim 10, wherein a total exposure time for both said first microwave image and said second microwave image is substantially equivalent to an integration time of said microwave receiver.

* * * * *